United States Patent
Chen

[11] Patent Number: 5,813,766
[45] Date of Patent: Sep. 29, 1998

[54] FINGER TEMPERATURE INDICATING RING

[76] Inventor: Mei-Yen Chen, 3rd Floor, No. 16-4, Lane 10, Chung Hwa Road, Yung Kang City, Tainan Hsien, Taiwan

[21] Appl. No.: 909,886

[22] Filed: Aug. 12, 1997

[51] Int. Cl.[6] .............................. G01K 1/14; G01K 1/16; G01K 7/22; G08B 23/00
[52] U.S. Cl. ......................... 374/141; 374/183; 600/549; 63/1.13; 63/15; 340/407.1; 340/573
[58] Field of Search ...................... 63/1.13, 15; 600/549; 374/141, 183; 340/573, 407.1

[56] References Cited

U.S. PATENT DOCUMENTS

| | | |
|---|---|---|
| 3,572,316 | 3/1971 | Vogelman et al. ....................... 600/549 |
| 3,885,576 | 5/1975 | Symmes .................... 340/573 |
| 3,983,753 | 10/1976 | Greenleaf et al. ...................... 600/549 |
| 4,059,830 | 11/1977 | Threadgill ............................. 340/407.1 |
| 4,220,016 | 9/1980 | Frenger ........................................ 63/32 |
| 4,407,295 | 10/1983 | Stever et al. ............................. 600/549 |
| 4,459,645 | 7/1984 | Glatter ..................................... 63/1.13 |
| 5,275,019 | 1/1994 | Pagani ........................................ 63/15 |
| 5,362,966 | 11/1994 | Rosenthal et al. ...................... 600/310 |
| 5,694,939 | 12/1997 | Cowings .................................... 600/27 |

FOREIGN PATENT DOCUMENTS

| | | |
|---|---|---|
| 57-11633 | 1/1982 | Japan ..................................... 374/141 |
| 0183919 | 8/1991 | Japan ..................................... 374/141 |
| 1591038 | 6/1981 | United Kingdom ................... 374/141 |
| 2200998 | 8/1988 | United Kingdom ................... 374/141 |

*Primary Examiner*—Diego F. F. Gutierrez
*Attorney, Agent, or Firm*—Rosenberg, Klein & Bilker

[57] ABSTRACT

A finger temperature indicating ring for wearing around a finger to measure and indicate the finger temperature of the wearer. A thermal conductive rod made of highly thermal conductive material, such as platinum, is provided in the ring with a lower end of the rod exposed from the ring to contact with the finger. The finger's heat or cold is accurately and quickly transmitted to a thermistor provided with the ring via the thermal conductive rod, causing a circuit connected to the thermistor to operate and convert the finger temperature into a signal which is sent to an indicating element in the ring. With a switch button, the signal can be presented to the wearer in different manners, so that the wearer is always reminded and encouraged to release himself or herself from physical or mental stress.

2 Claims, 2 Drawing Sheets

FINGER TEMPERATURE INDICATING RING

BACKGROUND OF THE INVENTION

Following the quick modernization and economic development, people face more and more stress in their daily life. As a result, psychiatric problems, such as insomnia, neurosis, psychosis, and psychosomatic disorders (including migraine, peptic ulcer, tension headache, etc.) become more and more common among people. According to statistic data, there are about 5 to 15 percents of adults suffering from such problems.

Our physical body and mind are interactive. Physical diseases may cause mental disorders. And mental discomfort may have adverse influence on physical health. When a person is subject to stress beyond what he or she can stand, physical or mental disorders may therefore develop. The mechanism is that the stress, when our brain senses it, may cause dysfunction of our autonomic nervous system, endocrine system, and immune system via the effect of neurological pathways.

The symptoms of anxiety caused by autonomic nervous system dysfunction may be: palpitation, dyspnea, chest tightness, dizziness, headache, dry mouth, gastro-intestinal tract upset, diarrhea, constipation, urinary frequency, tremor, perspiration, and cold limbs etc. Cold limbs are due to vasoconstriction of vessels. And clinically fingertip temperature has been used as a general and sensitive index to monitor if someone is relaxed or not. In short, when one is relaxed, his vessels will be dilated and his fingertip will be warmer. If one was anxious and tense, the vessels will be constricted and his fingertip will be cooler.

In clinical practice, medical doctors may instruct patients how to do muscle relaxation, and with the help of a biofeedback machine, they monitor patients to confirm that they are practicing muscle relaxation in the right way. What is more important is, of course, to find a way to detect an emotional tension caused by stress, so that such tension can be timely removed and overcome.

In the conventional method of measuring fingertip temperature used in a clinic, the biofeedback machine is large and expensive. It has a sensor which contacts the patient's skin to detect the fingertip temperature. The measured temperature value is converted into an electronic signal which is presented on a monitor to tell the patient if he was in a relaxed condition. Since it is impossible that medical staff or a large machine are always readily available for the patients, it is desirable to develop an auxiliary medical instrument which can be conveniently worn by the people and help the wearers relax or adjust themselves at any time.

SUMMARY OF THE INVENTION

It is therefore a primary object of the present invention to provide a finger temperature indicating ring which can be put on a finger of the wearer at any time to serve as an auxiliary medical instrument to effectively sense and indicate the wearer's finger temperature which reflects a physical and/or mental relaxing condition of the wearer, so as to help the wearer, either a psychiatric patient or a general user, to timely control or adjust his or her emotional condition.

BRIEF DESCRIPTION OF THE DRAWINGS

The structure and features of the present invention can be best understood from the following detailed description of the preferred embodiment and the accompanying drawings, wherein.

DETAILED DESCRIPTION OF THE PREFERRED EMBODIMENT

Figure 1:
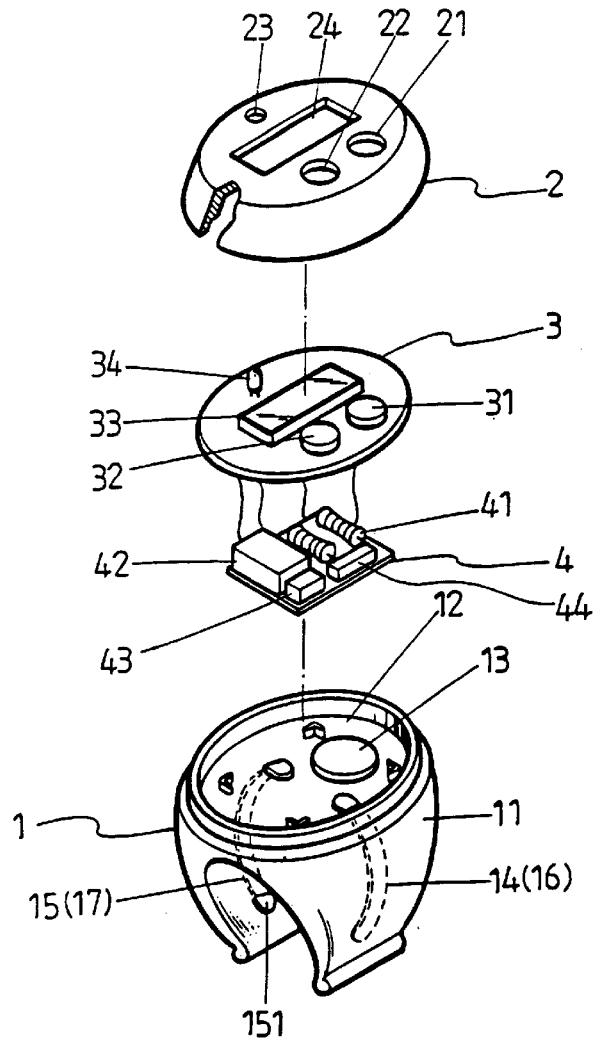
FIG. 1 is an exploded perspective of the present invention.
Figure 2:
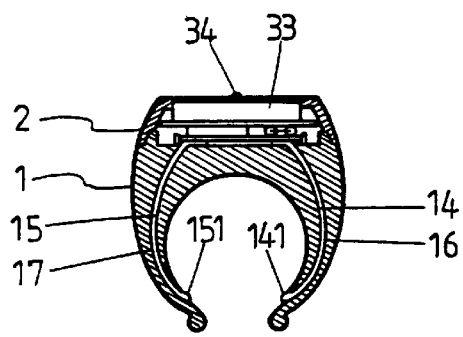
FIG. 2 is a sectional view showing the present invention in an assembled state.

Please refer to FIGS. 1 and 2 at the same time. The present invention relates to a finger temperature indicating ring which may sense and measure a wearer's finger temperature to indicate an undesirable mentally tense or stressed condition so that the wearer may timely and properly relax himself or herself. The finger temperature indicating ring mainly includes a ring body 1, a top cover 2 fitly covered on a top face of the ring body 1, a top panel 3 disposed between the ring body 1 and the top cover 2, and a circuit board 4 electrically connected to a bottom side of the top panel 3.

The ring body 1 includes a band portion 11 having a downward facing opening forming two lower ends of the ring body. Two symmetric channels 16, 17 are circumferentially embedded in two opposite sides of the band portion 11. The channels 16, 17 respectively receive an arcuated thermal conductive rod 14 and an arcuated discharge rod 15 therein. The thermal conductive rod 14 and the discharge rod 15 have lower ends which respectively project from an inner side of the two lower ends of the ring body 1, forming two exposed ends 141 and 151, respectively. The exposed ends 141 and 151 project from the inner side of the band portion 11 to such an extent that they can just touch an outer periphery of the wearer's finger when the ring of the present invention is worn around the finger. A top of the band portion 11 forms a shallow recess 12 in which a cell 13 and other electronic elements are located.

The top cover 2 has a contour corresponding to that of the recess 12 on the top of the ring body 1 and can therefore be placed onto the ring body 1 to fitly engage with the recess 12. The top cover 2 is formed at a top surface with several openings 21, 22, 23, and 24.

The top panel 3 is disposed in a space defined between the top cover 2 and top recess 12 of the ring body 1 when they are engaged with one another. A switch button 31, an on/off button 32, a liquid crystal display 33, and an LED 34 are provided on an upper surface of the top panel 3 and respectively project from the openings 21, 22, 23, and 24 formed on the top cover 2.

The circuit board 4 mainly includes a thermistor 41, an indicating element 42, a vibration motor 43, a buzzer 44, and other relevant electronic elements. Wherein, the thermistor 41 is connected to a top end of the thermal conductive rod 14. Since the thermal conductive rod 14 has an exposed end 141 which contacts with the finger skin, finger temperature can be sensed by the thermistor 41 via the thermal conductive rod 14. The finger temperature sensed by the thermistor 41 shall actuate an operation in the circuit board 4 and is converted into a signal which is sent to the indicating element 42. By using the switch button 31, one or more of the following manners can be selected to present the signal sent to the indicating element 42:

1. Cause the discharge rod 15 to discharge a small amount of electric current strong enough for the ring wearer to perceive;
2. Cause the liquid crystal display 33 to show the sensed finger temperature value;
3. Cause the LED 34 to emit light; or 4. Warn the ring wearer by other equivalent element, such as a vibration motor 43 or a buzzer 44, or both.

Figure 3:
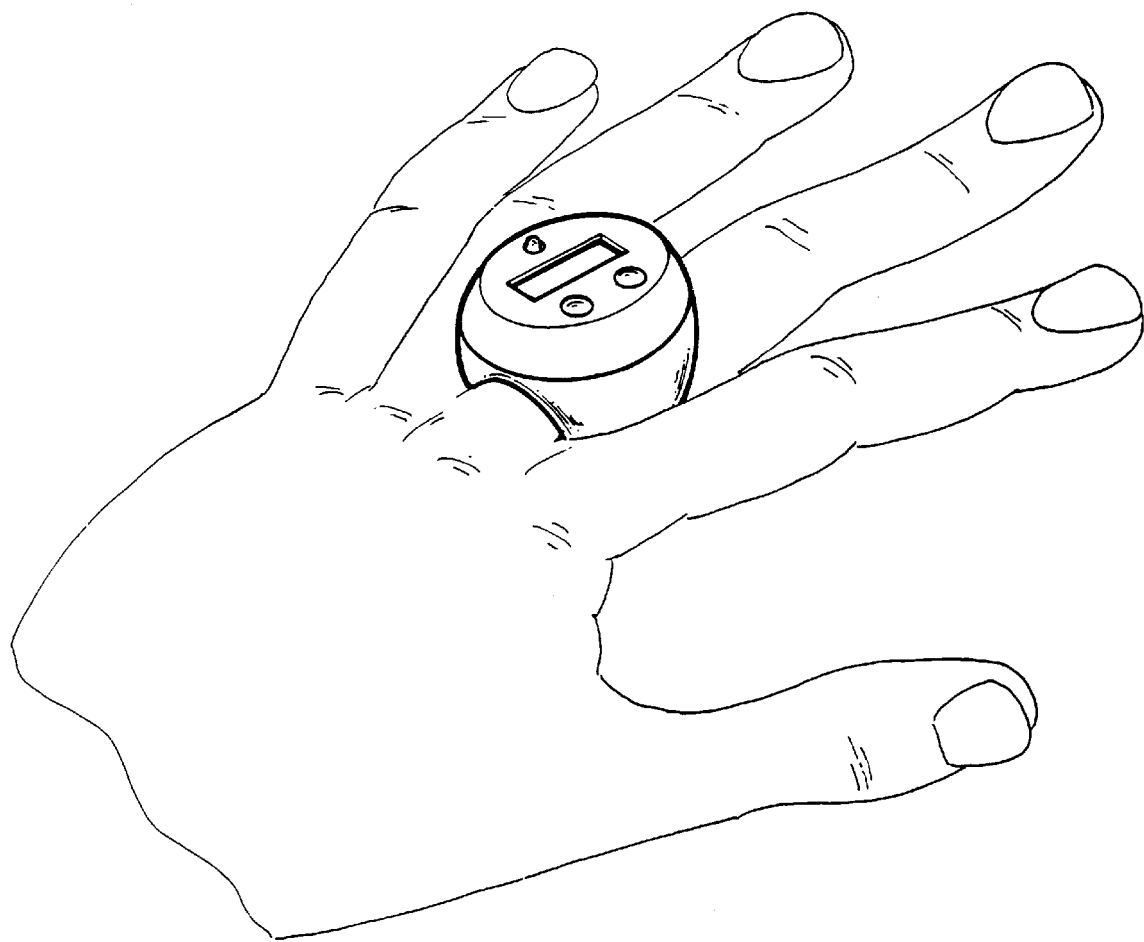
FIG. 3 illustrates a finger temperature indicating ring according to the present invention being put around a wearer's finger.

Please now refer to FIG. 3. To use the finger temperature indicating ring of the present invention, simply extend a finger through the band portion 11 of the ring body 1, so that the ring is worn around the wearer's finger. At this point, the exposed end 141 of the arcuated thermal conductive rod 14 near the lower inner side of the band portion 11 shall be slightly in contact with the wearer's finger. The thermal conductive rod 14 may be made of material with high thermal conductivity, such as platinum, to accurately and quickly transmit the finger's heat or cold to the thermistor 41. In the circuit board 4 which is not a subject matter of the present invention, an operation can be actuated by the sensed finger temperature to convert the temperature value into a signal. The signal is sent to the indicating element 42 and be presented to the ring wearer in a selected manner. There are different manners to present the signal, including figures displayed via the liquid crystal display 33, light emitted by the LED 34, a minor amount of current discharged by the arcuated discharge rod 15, or using any other equivalent means, such as a vibrator, buzzer, etc. With the signal, the wearer can be informed an objective value reflecting his or her current finger temperature. However, it is emphasized that the present invention is not designed to negatively warn the wearer but to positively encourage. So when the temperature is down (it means he/she is more anxious and tense), the instrument is silent. But when the temperature is raised, it will present a signal to tell the wearer that he/she is being in a more relaxed condition.

From the above description about the structure and the function of the present invention, it becomes clear the present invention has advantageously simplified the bulky and complicate instruments used in clinical therapy to measure a patient's finger temperature. The present invention is suitable for wearing by a patient or a general user at any time to always remind the wearer to relax so as to avoid any discomfort caused by physical and mental tension. The wearer may therefore always maintain a refreshing and stable condition. For a patient who suffers from psychiatric illness and therefore frequently needs to relax himself or herself, the ring of the present invention shall timely help the patient.

What is to be noted is the form of the present invention shown and disclosed is to be taken as a preferred embodiment of the invention and that various changes in the shape, size, and arrangements of parts may be resorted to without departing from the spirit of the invention or the scope of the subjoined claims.

What is claimed is:

1. A finger temperature indicating ring for indicating a physically or mentally relaxed condition of a wearer, comprising:

a ring body including a band portion having a lower opening forming two lower ends of said ring body, and two symmetric channels circumferentially embedded in two opposite sides of said band portion to respectively receive an arcuated thermal conductive rod and an arcuated discharge rod therein, said thermal conductive rod and said discharge rod having lower ends which respectively project from an inner side of said two lower ends of said ring body, forming two exposed ends to touch an outer periphery of the wearer's finger when said finger temperature indicating ring is worn around the wearer's finger; and said band portion having a shallow top recess for accommodating electronic elements of said ring therein;

a top cover having a contour corresponding to a contour of said top recess on said ring body for fitly covering said ring body and engaging with said top recess, and said top cover being formed at a top surface with several openings;

a top panel being disposed in a space defined between said top cover and said top recess of said ring body, said top panel being provided at an upper surface with a switch button, an on/off button, a liquid crystal display, and an LED which respectively project from said openings formed on said top cover; and a circuit board electrically connected to a bottom side of said top panal and including a thermistor, an indicating element, and other relevant electronic elements; wherein said thermistor is connected to a top end of said thermal conductive rod and may therefore sense a finger temperature of the wearer via said exposed end of said thermal conductive rod and actuate an operation in said circuit board to convert said finger temperature sensed by said thermistor into a signal, said signal corresponding to said physically or mentally relaxed condition of the wearer and being sent to said indicating element which presents said signal to the wearer in at least one of the following manners selected via said switch button on said top panel:

a. causing said discharge rod to discharge a small amount of electric current strong enough for the ring wearer to perceive it;

b. causing said liquid crystal display to show a value of said finger temperature sensed by said thermistor;

c. causing said LED to emit light; or d. warning the ring wearer by other equivalent element.

2. A finger temperature indicating ring as claimed in claim 1, wherein said other equivalent element for warning the ring wearer include one of a buzzer or a vibration motor, or both.

* * * * *